Figure 1:
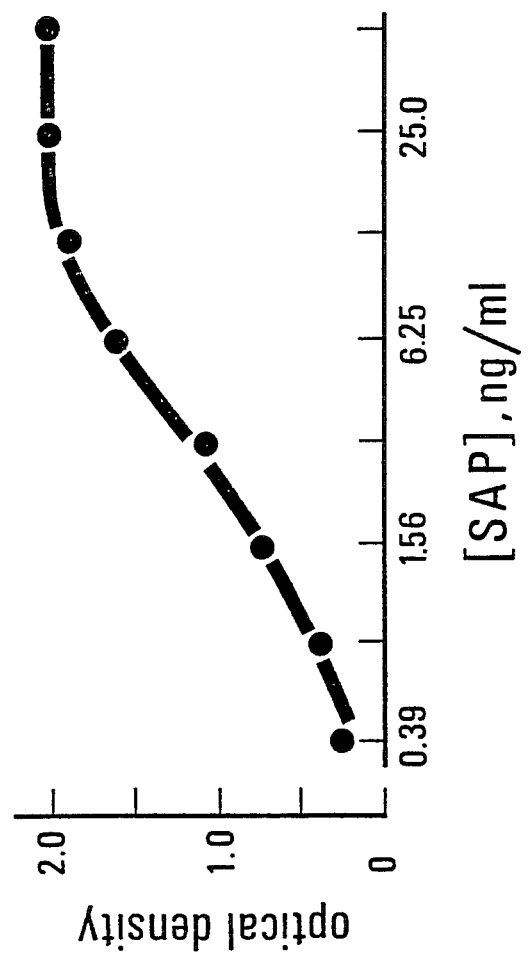

United States Patent [19]

Serban et al.

[11] Patent Number: 4,782,014

[45] Date of Patent: Nov. 1, 1988

[54] ASSAY AND PURIFICATION OF AMYLOID COMPONENTS, APPLICATIONS, AND KITS THEREFOR

[75] Inventors: Dan Serban, Binningen; Christiane Rordorf, Riehen, both of Switzerland

[73] Assignee: Ciba-Geigy Corporation, Ardsley, N.Y.

[21] Appl. No.: 874,771

[22] Filed: Jun. 16, 1986

[30] Foreign Application Priority Data

Jun. 25, 1985 [GB] United Kingdom ............... 8516081

[51] Int. Cl.⁴ .................... G01N 33/53; G01N 33/577
[52] U.S. Cl. ......................................... 435/7; 435/805;
435/810; 436/501; 436/528; 436/529; 436/530;
436/531; 436/532; 436/533; 436/534; 436/518;
436/808; 436/809; 436/810; 436/815; 530/386;
530/395; 530/411; 530/412; 530/415; 530/812;
530/813; 530/814
[58] Field of Search .................... 435/7, 805, 810;
436/501, 528–534, 548, 808–810, 815; 530/386,
395, 411, 412, 415, 812–816

[56] References Cited

U.S. PATENT DOCUMENTS

| | | | |
|---|---|---|---|
| 4,264,766 | 4/1981 | Fischer | 436/529 |
| 4,302,386 | 11/1981 | Stevens | 424/89 |
| 4,384,995 | 5/1983 | Stevens | 424/85 |
| 4,504,585 | 3/1985 | Reynolds | 436/518 |
| 4,666,829 | 5/1987 | Glenner et al. | 436/501 |
| 4,677,057 | 6/1987 | Curtiss et al. | 436/533 |
| 4,683,135 | 7/1987 | Pecht et al. | 424/88 |

OTHER PUBLICATIONS

Serban et al., J. Immunol., 135:3122–3127 (1985).
Painter et al., Annals New York Academy of Sciences vol. 389 (1982) pp. 199–215.
Lensen et al., Journal of Chromatography vol. 376 (1986) pp. 191–198.
Serban et al., Journal of Immunological Methods vol. 90 (1986) pp. 159–164.
G. Marhaug, scan. J. Immunol. 18, 329–338 (1983).
Chambers et al., J. of Immunol. Methods 59, pp. 95–103 (1983).
Hind et al., J. Exp. Med. 159, pp. 1058–1069 (1984).
Skinner et al. Ann. New York Acad. Sci. 389, pp. 190–198 (1982).
Maury et al., J. Lab. Clin. Med. 106, pp. 619–623 (1985).

Primary Examiner—Christine M. Nucker
Attorney, Agent, or Firm—Irving M. Fishman

[57] ABSTRACT

The invention relates to a new method of immunological analysis for serum amyloid A protein (SAA) and serum amyloid P-component (SAP), kits therefor and a method of purification of SAA and SAP. These methods are based on the efficient binding of SAP to a plastic surface and to carriers bearing nitrated phenyl groups in the presence of calcium and related bivalent ions, and of SAA to a plastic surface and to carriers bearing nitrated phenyl groups with or without calcium ions. The method of immunological analysis allows for rapid and reliable screening of serum samples with a high sensitivity. SAA and SAP play a key role in the diagnosis and management of inflammatory diseases.

24 Claims, 1 Drawing Sheet

ASSAY AND PURIFICATION OF AMYLOID COMPONENTS, APPLICATIONS, AND KITS THEREFOR

The invention relates to a new method of immunological analysis for serum amyloid A protein (SAA) and serum amyloid P-component (SAP), kits therefor and a method of purification of SAA and SAP.

BACKGROUND OF THE INVENTION

Following most forms of tissue injury, infection or inflammation, the concentrations of a number of plasma proteins increase, and then return to normal again as healing or recovery occurs. This process is known aas the acute phase response. In individuals with chronic inflammation, high levels of some acute phase proteins may persist.

Examples of acute phase reactants are C-reactive portein (CRP) and serum amyloid A protein (SAA). SAA is an $\alpha_1$ globulin consisting of a single polypeptide chain of molecular weight between 11'500 and 14'000 Dalton. Its plasma concentration, which is normally around 1 $\mu$g/ml or below in healthy individuals, increases substantially within few days following tissue injury or exposure to inflammatory stimuli. Related to the acute phase reactant CRP is serum amyloid P-component (SAP), a 9.5S $\alpha_1$ glycoprotein of 235'000 Dalton molecular weight. Whereas mouse SAP concentration substantially increases in inflammation, human SAP is not a major acute phase reactant, although its level can be moderately increased in some chronic inflammatory diseases and malignancies [M. B. Pepys, Clinics in Immunology and Allergy, Vol. 1, p. 77–101 (1981)].

SAP and SAA are synthesized by hepatocytes after stimuli from activated macrophages. The SAA and SAP inducing factor has been shown to be similar if not identicl to the monokine interleukin-1.

SAA and SAP are immunologically identical with amuloid A fibrils and amyloid P-component, respectively, found as constituents of all amyloidosis deposits. Amyloidosis is a disease which occurs secondary to a chronic inflammation.

Changes in concentration and ratio of acute phase proteins, e.g. CRP and SAA, and of SAP are important for diagnosis and management purposes of a number of acute and chronic inflammatory diseases such as rheumatic conditions, e.g. rheumatoid arthritis, juvenile polyarthritis, ankylosing spondylitis, Reiter's syndrome, psoriatic arthritis or rheumatic fever, vasculitis syndromes, Chron's disease, autoimmune conditions, e.g. systemic lupus erythematosus or polymyositis, malignancies, transplant rejection and the like.

The usual test for measuring changes in actue phase and related proteins until recently has been the erythrocyte sedimentation rate. This test is cheap and easily performed, but as an indirect method, not very accurate and reproducible. With the development of antisera directed against these proteins, it is now possible to measure individual components of the acute phase response and gain valuable information for diagnostic purposes. CRP has been and is still the acute phase reactant most widely measured. But recent data suggest that SAA is a more sensitive marker of inflammation than CRP [R. E. Chambers et al., Annals of the Rheumatic Diseases, 42, 665 (1983)]. It is also becoming evident that not all acute phase proteins are raised in parallel and that further valuable information can be obtained from the assessment of the SAP level in plasma.

The known techniques for SAA quantification basically are radioimmunoassays (RIA) and enzyme-linked immunosorbent assays (ELISA) [G. Marhaug, Scand. J. Immunol. 18, 329 (1983)]. These assays in their present form are not very sensitive and lack high reproducibility. There is a need for a more sensitive and reliable assay which allows the determination of SAA in a minimal amount of serum with simple and safe reagents in the whole concentration range of 0.1 $\mu$g/ml up to 2000 $\mu$g/ml.

SAP usually is measured by rocket immunoelectrophoresis, by indirect competitive ELISA (requiring large amounts of purified SAP) or by competitive RIA (requiring the preparation and handling of radioactive material). All these techniques are not sufficiently sensitive and require large amounts of serum hampering routine analysis. A sensitive method is therefore required which allows the measurement of SAP in a small amount of serum in a safe and reproducible manner in a concentration range of 1 $\mu$g/ml to 100 $\mu$g/ml in serum.

DESCRIPTION OF THE INVENTION

Surprisingly it is found that serum amyloid P-component (SAP) binds to a plastic surface in the presence of calcium ions and related bivalent ions such as zinc and cupric ions and, more efficiently, to organic or inorganic carriers bearing nitrated phenyl groups in the presence of calcium ions or related bivalent ions. Further it is found that serum amyloid A protein (SAA) binds to a plastic surface and, more efficiently, to organic or inorganic carriers bearing nitrated phenyl groups, optionally without or in the presence of calcium, zinc or related bivalent ions. This preferential binding of SAA and SAP to a plastic surface and to a carrier bearing nitrated phenyl groups, also in the presence of a large excess of irrelevant protein, is the basis of the method of immunological analysis for SAA and SAP of the present invention.

The present invention relates to a method of immunological analysis for serum amyloid A protein (SAA) and/or serum amyloid P-component (SAP), characterized in that SAA and SAP are bound to a plastic surface of a carrier or to a carrier bearing nitrated phenyl groups, whereby calcium or related bivalent ions have to be present for SAP binding.

In particular, the invention relates to a method of immunological analysis, wherein the plastic surface of a suitable carrier, e.g. of a microtiter plate, a test tube, a sheet, a bead or the like, is incubated with a solution containing SAA and/or SAP in the presence of calcium ions or related bivalent ions such as zinc and cupric ions, or with a solution containing SAA without additional ions, and the SAA and SAP bound to the plastic surface is detected and quantified by any of the usual techniques of immunoassays known per se. The carrier may be either plain plastic or any material coated with plastic. The plastic may be of natural, but is in particular of synthetic origin, e.g. a resinous polymeric organic substance such as polystyrene, polypropylene, polyethylene, polyvinyl chloride, polyvinyl acetate or the like. Binding of SAA and SAP to the plastic surface takes place also in the presence of an irrelevant protein added in excess, e.g. in the presence of excess bovine serum albumin added to saturate residual binding capacity of the plastic surface.

The invention relates particularly to a method of immunological analysis, wherein a suitable carrier, for example the plastic surface of a titre plate or of a test tube, for example of polystyrene, polypropylene or polyvinyl chloride, glass or plastic beads, filter paper, or dextran, cellulose acetate or nitrocellulose sheets or the like, is coated with a compound bearing nitrated phenyl groups, then incubated with a solution containing SAA and/or SAP in the presence of calcium ions, or with a solution containing SAA without calcium ions, and the SAA and SAP bound to the carrier is detected and quantified by any of the usual techniques of immunoassays known per se. The compound bearing nitrated phenyl groups may be a polypeptide, e.g. albumin, such as bovine serum albumin, keyhole limpet hemocyanin, casein, globulin or the like, a polysaccharide, e.g. dextran, starch, gelatin or cellulose, or a synthetic polymer, e.g. polyacryl hydrazide. A nitrated phenyl group is an o-, m- or p-nitrophenyl group, a dinitrophenyl group, e.g. a 2,4- or a 3,5-dinitrophenyl group, or a trinitrophenyl group, e.g. a 2,4,6-trinitrophenyl group.

Particularly preferred in the method of immunological analysis is a carrier coated with a compound bearing trinitrophenyl groups, e.g. 2,4,6-trinitrophenyl groups, in particular keyhole limpet hemocyanin bearing 2,4,6-trinitrophenyl groups. Efficient binding to this preferred carrier is observed also in the presence of excess irrelevant protein.

The preparation of compounds bearing nitrated phenyl groups is well known in the art. The compound bearing nitrated phenyl groups is coated onto the carrier by simple adsorption or optionally after activation of the carrier, for example with glutaraldehyde.

Immunological techniques to detect and quantify SAA or SAP bound to a carrier are well known in the art and are e.g. those typically used in enzyme immunoassays, radioimmunoassays or immunofluorescence assays. In particular, the carrier bearing bound SAA and/or SAP is treated with an antiserum or a monoclonal antibody specific for SAA or specific for SAP. This monoclonal antibody or the polyclonal antibodies of the antiserum may be suitably labelled, e.g. with a radioisotope, an enzyme or a fluorescing compound, and measured directly or after development with a suitable enzyme substrate. Otherwise, the unlabelled antiserum or monoclonal antibody is detected with a suitable labelled second antibody, preferably polyclonal antiserum against immunoglobulins of the animal species from which the first antiserum or monoclonal antibody is derived. Many variations of these principles of immunological analysis are known in the art, and the invention covers also assay procedures following a different routine for the detection of a specific compound.

The preferred method of immunological analysis is an enzyme-linked immunoadsorbent assay (ELISA), in which a carrier is coated with a polypeptide, polysaccharide or synthetic organic polymer bearing nitrated phenyl groups, preferably trinitrophenyl groups, then incubated with a solution containing SAA and/or SAP in the presence of calcium ions, or with a solution containing SAA without calcium ions, followed by a specific antiserum or a solution of monoclonal antibodies binding to the SAA or to the SAP. The bound monoclonal antibodies or polyclonal antibodies of the antiserum are then detected by a second antibody contained in a polyclonal antiserum against immunoglobulins of the animal species from which the first antiserum or monoclonal antibody is derived, wherein this second antibody is conjugated with an enzyme. The amount of second, enzyme-conjugated antibody bound is made visible and measured by development with an enzyme substrate. Instead of enzyme-labelled antibodies, it is also possible to use antibody-biotin conjugates together with avidin-enzyme conjugates.

Examples of enzymes useful in the method of the invention are horseradish peroxidase, alkaline phosphatase, $\beta$-D-galactosidase, glucose oxidase, glucoamylase, carbonic anhydrase, acetylcholineesterase, lysozyme, malate dehydrogenase, glucose-6-phosphate dehydrogenase or urease. Preferred enzymes are horseradish peroxidase which can be developed, for example, with the enzyme substrates 5-aminosalicylic acid, o-phenylenediamine, 3,3'-dimethoxy-benzidine, 3,3',5,5'-tetramethylbenzidine, 2,2'-azino-bis-(3-ethylbenzothiazoline-6-sulphonic acid) or the like and hydrogen peroxide, and alkaline phosphatase which, for example, releases p-nitrophenol from the enzyme substrate p-nitrophenyl phosphate.

In a preferred radioimmunoassay or a preferred immunofluorescence assay according to the invention, the same steps are performed as described above for a preferred ELISA, with the exception that the second antibody is radiolabelled, e.g. with $^{125}$I, or conjugated to a fluorescing compound, e.g. to fluorescein, respectively, and that the development with enzyme substrate is omitted.

The immunoassays described can be used to determine the quantity of SAA and/or SAP in serum, especially human serum, on a routine basis using only small amounts of serum prepared from 0.1 ml or less of whole blood, facilitating the diagnosis and supervision of therapeutic treatment of acute and chronic inflammatory diseases.

The invention relates also to test kits for the qualitative and quantitative determination of SAA and/or SAP containing carriers and reagents suitable for an immunoassay as described above.

Test kits according to the invention for an ELISA contain, for example, a suitable carrier, e.g. a carrier having a plastic surface or a carrier coated with a polypeptide, polysaccharide or synthetic organic polymer bearing nitrophenyl groups, preferably trinitrophenyl groups, optionally solutions of a compound bearing nitrophenyl groups, preferably trinitrophenyl groups, solutions of a monoclonal or of polyclonal antibodies binding SAA or SAP, and, if said first antibodies are not labelled with an enzyme, solutions of polyclonal, enzyme-conjugated second antibodies binding said first antibodies, enzyme substrates in solid or dissolved form, standard solutions of SAA and/or SAP, buffer solutions and optionally calcium salts or related bivalent salts such as zinc or cupric salts in solid or dissolved form, and optionally pipettes, reaction vessels, calibration curves, colour intensity tables and the like. The solutions may be in concentrated form or freeze-dried requiring dilution with water or buffer solution before use.

Preferred test kits contain a carrier coated with a polypeptide bearing trinitrophenyl groups, e.g. a carrier coated with keyhole limpet hemocyanin bearing 2,4,6-trinitrophenyl groups.

Test kits according to the invention for a radioimmunoassay or an immunofluorescence assay may contain the same carriers, reagents and hardware as described above, but radiolabelled antibodies or antibodies conjugated with fluorescing compounds, respectively, replacing the enzyme-conjugated antibodies and the enzyme substrate.

The invention further relates to a method of purification of SAA and/or SAP by affinity chromatography on solid carriers bearing nitrated phenyl groups.

A carrier material on an inorganic or organic basis, for example silicates, crosslinked agarose, dextran, polyacrylamide or polyacrylhydrazide in suitably functionalized form, is reacted in a manner known per se with a reagent introducing nitrated phenyl groups, preferably trinitrophenyl groups. For example, a carrier material containing reactive carbonyl hydrazide functions is treated with 2,4,6-trinitrobenzenesulfonic acid introducing trinitrophenyl groups, or with 2,4-dinitrofluorobenzene introducing dinitrophenyl groups. Otherwise, a carrier material containing reactive ester functions e.g. N-hydroxysuccinimide ester groups, is treated with p-nitrophenylhydrazine or p-nitroaniline introducing nitrophenyl groups.

Preferred carrier material consists of crosslinked agarose bearing trinitrophenyl groups, e.g. 2,4,6-trinitrophenyl groups.

Such a carrier bearing nitrated phenyl groups is suspended in a suitable aqueous solvent containing calcium ions or related bivalent ions, such as zinc or cupric ions, for example saline containing calcium chloride, or a buffer solution contaning calcium chloride e.g. Tris(-tris[hydroxymethyl]aminomethane) buffered saline and calcium chloride. The solution containing SAP, e.g. serum or other biological fluids, is treated with a calcium salt, e.g. calcium chloride, or a salt containing a related bivalent ion, then brought into contact with the carrier bearing nitrated phenyl groups, e.g. by pouring it on top of a column containing the carrier and letting it flow through the carrier by gravity or external pressure. The SAP is retained on the carrier, whereas unbound proteins and other impurities are washed away with aqueous solutions containing calcium ions or similar bivalent ions, for example Tris buffered saline containing calcium chloride. The SAP is eluted with suitable aqueous solutions containing ion chelators, e.g. saline or Tris buffered saline containing ethylenediaminetetraacetic acid or related chelating compounds, aqueous acids or buffer solutions in a pH range below pH 5, e.g. around pH 3, or buffer solutions containing p-nitrophenylarsonic acid.

For the purification of SAA, the carrier bearing nitrated phenyl groups preferably is treated with a zinc salt, e.g. zinc chloride, then washed with a buffer solution before the SAA containing solution, e.g. serum, is applied to it. The SAA is retained on the carrier, whereas other proteins and impurities are washed away with aqueous salt solutions, e.g. buffers, such as Tris buffered saline. The SAA is eluted with aqueous solutions containing detergents, e.g. Tris buffered saline containing 0.01% to 2% of a polyethylene glycol fatty alcohol ether, of a polyethylene glycol alkylphenol ether, of a polyoxyethylene sorbitan fatty acid ester or of a ionic detergent such as sodium dodecyl sulfate, or with aqueous acids or buffer solutions in a pH range below pH 5, e.g. around pH 3.

Optionally the purification procedure may be improved by pretreatment of the solution containing SAA and/or SAP on a solid carrier bearing nitrated phenyl groups, but in the absence of calcium, zinc or related bivalent ions, or pre- or aftertreatment with immunoadsorbent carriers bearing antibodies specific for a contaminant, e.g. specific for immunoglobulins.

SAA and SAP are isolated from the purified solutions according to methods known per se, for example chromatography over Sephadex ®, dialysis, electrophoretic concentration and the like.

The following Examples illustrate the invention without, however, limiting the scope thereof in any way.

Abbreviations

BSA: bovine serum albumin
DNP: dinitrophenyl
EDTA: ethylenediamine-N,N,N',N'-tetraacetic acid
EGTA: 1,2-di(2-aminoethoxy)ethane-N,N,N',N'-tetraacetic acid
ELISA: enzyme-linked immunosorbent assay
FSC: fluoresceinyl
Ig: immunoglobulin
KLH: keyhole limpet hemocyanin
PAH: polyacryl hydrazide
PC: phosphorylcholine
SAA: serum amyloid A protein
SAP: serum amyloid P-component
TBS: Tris buffered saline
TNP: trinitrophenyl
Tris: tris(hydroxymethyl)aminomethane

EXAMPLE 1

TNP-derivatized polypeptides 11 ml of a KLH slurry in 65% ammonium sulfate (18 mg/ml, Calbiochem-Behring, La Jolla CA, USA) are diluted with 4 ml water, dialyzed versus 0.15M NaCl/25 mM NaHCO$_3$, then centrifuged at 2'000×g for 10 minutes. The supernatant is diluted to 25 ml with 0.1M NaHCO$_3$, and half of it (12.5 ml, 8 mg KLH per ml) mixed with a solution of 12 mg 2,4,6-truinitrobenzenesulfonic acid (Fluka, Buchs, Switzerland) in 1 ml 0.3M NaHCO$_3$. After 4 hours in the dark at 37° C., the mixture is dialyzed versus saline containing 25 mM NaHCO$_3$ and filtered through a 0.45 μm filter (Millex ®-HA-filter, Millipore). The resulting conjugate contains 43 TNP residues per 100'000 Dalton KLH and may be kept in the frozen state for an extended period of time without deterioration.

Similarly TNP-BSA is prepared from BSA (Merck, Darmstadt, W. Germany) and 2,4,6-trinitrobenzenesulfonic acid yielding a conjugate with 15 TNP residues per BSA molecule.

EXAMPLE 2

ELISA for SAP

The wells of flat-bottom polystyrene microtiter plates (Immulon ®, Dynatech, Zug, Switzerland) or polyvinyl chloride microtiter plates (Microtest III ™, Becton Dickinson, Oxnard, CA, USA) are incubated with either 100 μl 0.3M NaHCO$_3$ alone, 100 μl KLH 2 μg/ml in 0.3M NaHCO$_3$, or 100 μl TNP-KLH (Example 1) 2 μg/ml in 0.3M NaHCO$_3$ for one hour or more at room temperature. The plates coated with TNP-KLH may be stored at room temperature after drying with a hot-air blower without loss of binding capacity. The plates are washed with 5 mM CaCl$_2$, then incubated with 100 μl each of human SAP containing samples (standard solutions or serum dilutions in ELISA buffer) for 2 hours at 20° C. ELISA buffer consists of TBS (20 mM Tris-HCl, pH 7.8, 0.14M NaCl) containing 0.5% BSA, 0.05% merthiolate (Thimerosal ™) and 5 mM CaCl$_2$. The plates are washed with 5 mM $CaCl_2$, incubated for 2 hours at 20° C. with 100 μl of rabbit antiserum to human SAP (Calbiochem) diluted 1:10⁴ with ELISA buffer, washed again with 5 mM $CaCl_2$, and incubated overnight in a water-saturated atmosphere at 20° C. with 100 μl of horseradish peroxidase conjugated donkey anti-rabbit Ig antiserum (Amersham Int., Amersham, UK) diluted 1:5000 with ELISA buffer. The plates are washed, then developed with 100 μl per well of buffered o-phenylenediamine (100 mg in 48.6 ml 0.1M citric acid and 51.4 ml 0.2M $Na_2HPO_4$, pH 5.0) containing 0.03% $H_2O_2$ in the dark at 20° C. for 15 minutes. The reaction is stopped by addition of 25 μl 2.5M $H_2SO_4$ and the optical density of the colour developed by the enzyme reaction determined at 492 nm using a Titertek ® multiscan spectrophotometer (Flow Laboratories).

The same procedure can be used for the detection of mouse SAP, if the corresponding antiserum to mouse SAP is used.

SAP binds to polystyrene and polyvinyl chloride surface after treatment with $Ca^{2+}$ ions. More efficient binding is obtained by coating the plastic surface with trinitrophenylated macromolecules, e.g. TNP-KLH (Table 1).

The presence of 0.25 mM or more $CaCl_2$ in all incubation solutions and washings is essential. A sharp decrease of SAP binding is observed with 0.12 mM $CaCl_2$, and no SAP is bound at 0.06 mM or lower concentrations of $CaCl_2$.

TABLE 1

Binding of purified human SAP to uncoated ($Ca^{2+}$ treated), KLH coated and TNP-KLH coated plastic surface.

| pg SAP in sample (100 μl) | optical density at 492 nm | | | | | |
|---|---|---|---|---|---|---|
| | polystyrene coated with | | | polyvinyl chloride coated with | | |
| | $Ca^{2+}$ only | KLH | TNP-KLH | $Ca^{2+}$ only | KLH | TNP-KLH |
| 5'000 | 1.80 | 1.70 | 1.90 | 1.85 | 1.60 | >2.0 |
| 2'500 | 1.60 | 1.50 | 2.0 | 1.65 | 1.60 | >2.0 |
| 1'250 | 0.94 | 1.40 | 1.90 | 1.10 | 1.20 | >2.0 |
| 625 | 0.61 | 0.95 | 1.60 | 0.72 | 0.83 | >2.0 |
| 312 | 0.45 | 0.48 | 1.10 | 0.53 | 0.57 | 1.95 |
| 156 | 0.29 | 0.40 | 0.75 | 0.29 | 0.34 | 1.25 |
| 78 | 0.18 | 0.20 | 0.43 | 0.19 | 0.19 | 0.80 |
| 39 | 0.0 | 0.15 | 0.30 | 0.12 | 0.13 | 0.53 |

FIG. 1 demonstrates that with TNP-KLH coated polystyrene plates a linear dependence of optical density from SAP concentration is obtained in a range of 0.5 to 10 ng/ml. The sensitivity of the assay therefore allows the reliable detection of SAP in normal human serum down to a dilution of 1 to $2 \times 10^4$.

In the preferred version of the ELISA for SAP, polystyrene microtiter plates coated with TNP-KLH are used.

EXAMPLE 3

Test kit for SAP-ELISA

A test kit for the enzyme-linked immunoassay described in Example 2 contains:
polystyrene microtiter plates
20 ml of TNP-KLH (Example 1), 2 μg/ml in 0.3M $NaHCO_3$, or polystyrene microtiter plates coated with TNP-KLH (Example 2)
1 ml of SAP standard solution 50 ng/ml in ELISA buffer
20 ml of rabbit antiserum to human SAP diluted 1:10⁴
20 ml of horseradish peroxidase conjugated donkey anti-rabbit Ig antiserum diluted 1:5'000
20 ml of o-phenylenediamine (10 mg/ml) in citrate-/phosphate buffer pH 5.0
1 ml of $H_2O_2$ 3%
200 ml of 5 mM calcium chloride

EXAMPLE 4

Inhibition of binding of SAP to TNP-KLH coated polystyrene

The procedure of Example 2 is followed, using polystyrene microtiter plates coated with TNP-KLH. The samples containing 40 ng/ml human SAP are preincubated with dilutions of the compound to be tested as an inhibitor for two hours at 20° C. The perent decrease in SAP binding to TNP-KLH is calculated in comparison to the SAP binding in the absence of any inhibitor. The concentration of the inhibitor resulting in half-maximal (50%) inhibition of SAP binding is given in Table 2.

TABLE 2

Inhibitor concentration resulting in 50% inhibition of human SAP binding to TNP-KLH coated polystyrene.

| Substance | concentration at 50% inhibition |
|---|---|
| EDTA | 5.35 ± 1.3 mM |
| EGTA | 17.0 ± 2.2 mM |
| iminodiacetic acid | N.I.[a] |
| arsanilic acid (p-aminophenylarsonic acid) | 27.3 ± 4.9 mM |
| p-nitrophenylarsonic acid | 4.2 ± 1.3 mM |
| phosphorylcholine (PC) | N.I. |
| picric acid (trinitrophenol) | 33.0 ± 3.8 mM |
| p-nitrobenzoic acid | N.I. |
| flavinic acid (2,4-dinitro-1-naphthol-7-sulphonic acid) | 43.3 ± 5.8 mM |
| dinitrophenol | N.I. |
| pectic acid | 0.2 ± 0.07 μg/ml |
| bovine serum albumin (BSA) | N.I. |
| polyacryl hyrazide (PAH) | N.I. |
| keyhole lympet hemocyanin (KLH) | 0.88 ± 0.32 μg/ml |
| ovalbumin | N.I. |
| PC-BSA | N.I. |
| DNP-BSA | N.I. |
| DNP-PAH | N.I. |
| TNP-BSA | 0.33 ± 0.06 μg/ml |
| TNP-PAH | 2.73 ± 0.31 μg/ml |
| TNP-KLH | 0.68 ± 0.32 μg/ml |
| Brij ® 35 | N.I. |
| Tween ® 20 | N.I. |

[a]No inhibition at 20 mM or 100 μg/ml

The binding of SAP to a TNP-KLH coated carrier requires $Ca^{2+}$ ions as described hereinbefore. It is therefore reasonable that EDTA and EGTA, efficient calcium chelators, are inhibitors of SAP binding at concentrations equal or in excess of the $Ca^{2+}$ concentration applied in the assay procedure.

As expected, trinitrophenylated polymers such as TNP-BSA, TNP-PAH and TNP-KLH, and to a lesser extent also trinitrophenol (picric acid), compete efficiently for SAP in an assay based on binding to TNP-KLH coated polystyrene. The binding of SAP to dinitrophenol and dinitrophenylated polymers is clearly weaker, and these compounds are no inhibitors in the present assay. Inhibiting properties are further observed with p-amino- and p-nitrophenylarsonic acid, flavinic acid, pectic acid, and KLH without trinitrophenyl functions. Two non-ionic detergents tested (Brij ®35 and Tween ®20) have no effect on SAP binding to TNP-KLH.

EXAMPLE 5

Elution of SAP bound to TNP-KLH coated polystyrene

Polystyrene microtiter plates coated with TNP-KLH as described in Example 2 are incubated with 20 ng of human SAP per well in 100 μl of ELISA buffer. After washing with 5 mM CaCl$_2$, the plates are incubated with dilutions of the inhibitors listed in Table 2 in 100 μl of ELISA buffer for 2 hours at 20° C. The microtiter plates are processed as described in Example 2, and the percent elution calculated relative to a SAP sample treated with ELISA buffer only. Significant elution was found only with EDTA (100% at 10 mM), p-nitrophenylarsonic acid (90% at 10 mM, 45% at 2 mM) and arsanilic acid (28% at 10 mM).

EXAMPLE 6

Purification of human SAP on a TNP-Sepharose column 70 g of Sepharose ®4B (Pharmacia, Uppsala, Sweden) are activated for 10 min at pH 11.2 with 7 g BrCN (Fluka) and reacted overnight at 4° C. with 870 mg adipic dihydrazide (Fluka). 40 ml of this ADH-Sepharose are resuspended in 50 ml 0.1N NaHCO$_3$ containing 630 mg 2,4,6-trinitrobenzenesulfonic acid and incubated at 20° C. overnight. The TNP-Sepharose is washed with water, 1M NaCl, 0.5M acetic acid and water, and kept at 4° C. in 0.1% aqueous NaN$_3$. A similar product can be obtained when the activated Sepharose ®4B is treated with 70 mg of PAH in place of adipic dihydrazide.

5 ml of normal human serum is applied to a column containing 5 ml of above TNP-Sepharose equilibrated with TBS. The column is eluted with TBS, and fractions containing protein are pooled. SAP is not retained on TNP-Sepharose in the absence of Ca$^{2+}$ ions. Solid CaCl$_2$ is added to the pooled fractions to make a 50 mM solution and this is applied to a second TNP-Sepharose column (5 ml) equilibrated with TBS containing 50 mM CaCl$_2$. The column is washed with 50 mM CaCl$_2$/TBS, and SAP eluted with TBS containing 100 mM EDTA, pH 7.8, by 0.5M acetic acid, or by TBS containing 10 mM p-nitrophenylarsonic acid.

From a total of 200 μg of SAP introduced, 189 μg are recovered in the final EDTA eluate (as measured in the ELISA of Example 2). The only contaminant detected is normal immunoglobulin, which is removed by affinity chromatography on columns with insolubilized protein A or anti-human immunoglobulin antibody.

If untreated Sepharose in place of TNP-Sepharose is used, 112 μg out of 200 μg SAP are washed out with 50 mM CaCl$_2$/TBS, and the final EDTA eluate contains only 82 μg SAP.

EXAMPLE 7

ELISA for SAA

The wells of polystyrene microtiter plates are coated with KLH, TNP-KLH or left uncoated as described in Example 2, then washed with 5 mM CaCl$_2$ and incubated with 100 μl each of human SAA containing samples obtained by serial dilutions of a patient's serum. After two hours at 20° C., the plates are washed with 5 mM CaCl$_2$, incubated with 100 μl of a rabbit antiserum to human SAA (Calbiochem) diluted 1:2500 in ELISA buffer, and developed with anti-rabbit serum conjugated to horseradish peroxidase as described in Example 2.

Human SAA binds to polystyrene coated with TNP-KLH very efficiently. Substantial binding is also observed to KLH-coated polystyrene and even to polystyrene alone (Table 3). Ca$^{2+}$ can be omitted without loss in binding efficiency to TNP-KLH coated polystyrene.

TABLE 3

Binding of human SAA to uncoated (Ca$^{2+}$ treated), KLH coated and TNP-KLH coated polystyrene

| dilution of serum[a] | optical density at 492 nm | | |
|---|---|---|---|
| | no coating (Ca$^{2+}$) | KLH-coated | TNP-KLH-coated |
| 1:625 | >2 | >2 | >2 |
| 1:1'250 | >2 | >2 | >2 |
| 1:2'500 | 1.70 | >2 | >2 |
| 1:5'000 | 1.15 | 1.7 | >2 |
| 1:10'000 | 0.67 | 1.05 | 1.75 |
| 1:20'000 | 0.39 | 0.71 | 0.97 |

[a]serum from a patient with rheumatoid arthritis

If a detergent such as Brij 35 ® is added to the buffer used for preparing SAA samples and the washings, the optical density is reduced to one tenth or less for a given SAA concentration.

In a preferred version of the ELISA for SAA, polystyrene microtiter plates coated with TNP-KLH are used.

EXAMPLE 8

Test kit for SAA-ELISA

A test kit for the enzyme-linked enzyme immunoassay described in Example 7 contains:
polystyrene microtiter plates
20 ml of TNP-KLH (Example 1), 2 μg/ml in 0.3M NaHCO$_3$, or polystyrene microtiter plates coated with TNP-KLH (Example 2)
1 ml of pooled serum from patients with rheumatoid arthritis diluted to approx. 10 μg/ml of SAA
20 ml of rabbit antiserum to human SAA diluted 1:2500
20 ml of horseradish peroxidase conjugated donkey anti-rabbit Ig antiserum diluted 1:5'000
20 ml of o-phenylenediamine (10 mg/ml) in citrate/phosphate buffer pH 5.0
1 ml of H$_2$O$_2$ 3%
200 ml of TBS

EXAMPLE 9

Purification of human SAA on a TNP-Sepharose column 6 ml of serum from rheumatic arthritis patients rich in SAA is applied to a column containing 5 ml of TNP-Sepharose (Example 6) pretreated with a solution of zinc chloride, then washed and equilibrated with TBS. After washing with TBS, the SAA is eluted with TBS containing 0.1% Brij 35 ®.

EXAMPLE 10

Determinatin of SAA and SAP in human serum

Human sera of different sources are analyzed for SAP and SAA using the ELISA described in Example 2 and Example 7 on polystyrene microtiter plates coated with TNP-KLH. The following results are obtained (Table 4):

TABLE 4

SAP and SAA content of human sera from different sources.

| Serum[a] | SAP (μg/ml) | SAA (units/ml) hu (B) |
|---|---|---|
| 417 | 48 | 825 |
| 487 | 53 | 18 |
| 522 | 60 | 21 |
| 523 | 94 | 19 |
| 543 | 38 | 18 |
| 554 | 54 | 33 |
| 558 | 65 | 22 |
| 250 | 39 | 19 |
| 350 | 51 | 23 |
| 520 | 71 | 17 |
| 527 | 39 | 34 |
| 530 | 62 | 29 |
| HF 1 | 52.4 | 186000 |
| 2 | 59.2 | 246000 |
| 3 | 30.5 | 165000 |
| 4 | 32.1 | 128000 |
| 5 | 27.0 | 74000 |
| 6 | 32.3 | 80200 |
| 7 | 33.3 | 17200 |
| 8 | 34.8 | 800 |
| SW 1 | 79.3 | 45400 |
| 2 | 64.5 | 22900 |
| M | 34.2 | 1700 |
| 89-65 | 30.7 | 6300 |
| 67 | 30.9 | 9100 |
| 98 | 34.9 | 5500 |
| 99 | 15.5 | 6000 |
| 90-00 | 43.7 | 5700 |
| 01 | 34.4 | 4900 |
| 04 | 34.4 | <780 |
| 17 | >50 | 6000 |
| 21 | 25.3 | 4800 |
| 24 | 18.6 | 5900 |
| 26 | 18.3 | 5100 |
| 27 | 46.0 | 5800 |
| 28 | 34.8 | 6600 |
| 36 | 18.5 | 4300 |
| 37 | >50 | 4800 |
| 40 | 34.5 | 5300 |
| 47 | 41.1 | 6500 |
| 58 | 40.4 | 6300 |
| 59 | 31.8 | 6600 |
| 61 | >50 | 9300 |
| 64 | 21.5 | 5300 |
| 68 | 28.0 | 5200 |
| 69 | >50 | 5700 |
| 72 | >50 | 6100 |
| 75 | 12.0 | 6900 |
| 91-25 | 39.7 | 18200 |
| 26 | >50 | >25000 |
| 27 | 36.4 | >25000 |
| 28 | 34.9 | >25000 |
| 39 | 49.5 | 7900 |
| 45 | >50 | 9000 |
| 53 | 37.3 | >25000 |
| 54 | 31.3 | 16600 |
| 73 | 27.4 | 11100 |
| 74 | >50 | 8500 |
| 75 | 21.2 | 3800 |
| 89 | 13.2 | 4300 |
| 92 | 15.8 | 3100 |
| 94 | >50 | 5600 |
| 95 | >50 | 3600 |
| 92-07 | 50.0 | 5900 |
| 13 | 31.7 | 9300 |
| 33 | 10.9 | >25000 |
| 39 | 36.9 | 4700 |
| 41 | 37.4 | 2400 |
| P1 | 9.4 | 39500 |
| 2 | 26.7 | 140500 |
| 3 | 16.0 | 2800 |
| 4 | 29.2 | 48700 |
| 5 | 11.7 | 18800 |
| 6 | 8.8 | 37500 |
| 7 | 40.25 | 57600 |
| 8 | 18.3 | 1500 |

[a]Source of the human serum
417-530 (three digit numbers): healthy volunteers
HF: patients with pneumonia
SW: patients with a disease related to systemic lupus erythematosus
M: patient with amyloidosis
89-65 to 92-41 (four digit numbers): patients with systemic lupus erythematosus
P: patients in emergency care after road accidents
[b]Pure human SAA is not available. 1 unit corresponds to (maximum) 7 ng of SAA. The standard used is a patient serum containing ca. 1 mg/ml SAA, arbitrarily assigned 140'000 units/ml.

The results presented in Table 4 demonstrate that the immunoassays of this invention are useful for the determination of SAP and SAA in sera of normal humans and in sera of patients with inflammatory conditions including systemic lupus erythematosus. No serum was found in which the SAP or SAA level was too low to be measured reliably by the disclosed method in routine analysis.

We claim:

1. A method of immunological analysis for serum amyloid A protein (SAA), comprising
    (a) binding said SAA to an organic or inorganic carrier bearing nitrated phenyl groups, and
    (b) detecting or detecting and quantifying said bound SAA,
said step b being accomplished by incubating said bound SAA with an antiserum or a first monoclonal antibody specific for SAA, said antiserum containing a second antibody for said SAA, said first and second antibodies being labelled or when not labelled, further incubating said bound SAA with said first or second antibody attached thereto with a second antiserum or third labelled monoclonal antibody specific for said first or second antibody and which further antiserum contains a labelled fourth antibody which is specific for said first or second antibody, and detecting or detecting and measuring the amount of labelled antibody bound to said carrier.

2. A method according to claim 1, wheren the label of the labelled antibodies is an enzyme measured by an enzyme/substrate reaction.

3. A method according to claim 1, wherein the carrier bearing nitrated phenyl groups is prepared by coating an organic or inorganic carrier with a compound bearing nitrated phenyl groups.

4. A method according to claim 1, wherein the carrier bearing nitrated phenyl groups is selected from the group consisting of a microtitre plate, a test bue, a sheet or a bead of polystyrene, polypropyle, and polyvinyl chloride, glass and plastic beads, filter paper, and dextran, cellulose acetate, and nitrocellulose sheets.

5. A method according to claim 3, wherein the compound bearing nitrated phenyl groups is a polypeptide, a polysaccharide or a synthetic polymer bearing nitrated phenyl groups.

6. A method according to claim 3, wherein the compound bearing nitrate phenyl groups is a polypeptide bearing nitrated phenyl groups.

7. A method according to claim 1, wherein the nitrated phenyl group is a nitrophenyl group, a dinitrophenyl group or a trinitrophenyl group.

8. A method according to claim 1, wherein the nitrated phenyl group is a 2,4,6-trinitrophenyl group.

9. A method according to claim 3, wherein the compound bearing nitrated phenyl groups is keyhole limpet hemocyanin bearing 2,4,6-trinitrophenyl groups.

10. A test kit for the qualitative or quantitative determination of SAA, comprising an organic or inorganic carrier coated with a compound bearing nitrophenyl groups, a solution of enzyme-labelled or unlabelled monoclonal or polyclonal first antibodies binding SAA, and, if said first antibodies are not labelled with an enzyme, then also a solution of polyclonal, enzyme-conjugated second antibodies binding said first antibodies, an enzyme substrate in solid or dissolved form, a standard solution of SAA, and a buffer solution.

11. A test kit according to claim 10, wherein said carrier is coated with keyhole limpet hemocyanin bearing 2,4,6-trinitrophenyl groups.

12. A method of purification of SAA comprising (a) bringing into contact a solution containing SAA with a solid carrier bearing nitrated phenyl groups pretreated with a zinc salt, (b) washing away unbound proteins and other impurities with an aqueous salt solution and (c) eluting said SAA with an aqueous solution containing a detergent, with aqueous acids, or with buffer solutions in a pH range below pH 5.

13. A method of immunological analysis for serum amyloid P-component (SAP), comprising binding SAP, in the presence of calcium ions, to an organic or inorganic carrier hearing nitrated phenyl groups, and detecting or detecting and quantifying said bound SAP by incubatating said bound SAP with first antiserum having a first antibody or with a monoclonal second antibody specific for SAP, wherein said first and second antibodies are labelled or said bound SAP with said first or second antibody attached thereto is further incubated with, antiserum containing a labelled third antibody or a monoclonal labelled fourth antibody, which third and fourth antidodies are specific or said first or second antibodies, and measuring the amount of said labelled antibody finally bound to the carrier.

14. A method according to claim 13, wherein the label of the labelled antibodies is an enzyme measured by an enzyme/substrate reaction.

15. A method according to claim 13, wherein the carrier bearing nitrated phenyl groups is prepared by coating an organic or inorganic carrier with a compound bearing nitrated phenyl groups.

16. A method according to claim 13, wherein the carrier bearing nitrated phenyl groups is selected from the group consisting of a microtitre plate a test tube, a sheet and a bead of polystyrene, polypropylene, and polyvinyl chloride, glass and plastic beads, filter paper, and dextran, cellulose acetate and nitrocellulose sheets.

17. A method according to claim 15, wherein the compound bearing nitrated phenyl groups is a polypeptide, a polysaccharide or a synthetic polymer bearing nitrated phenyl groups.

18. A method according to claim 15, wherein the compound bearing nitrated phenyl groups is a polypeptide bearing nitrated phenyl groups.

19. A method according to claim 13, wherein the nitrated phenyl group is a nitrophenyl group, a dinitrophenyl group or a trinitrophenyl group.

20. A method according to claim 13, wherein the compound bearing the nitrated phenyl group is keyhole limpet hemocyanin bearing 2,4,6-trinitrophenyl groups.

21. A method according to claim 15, wherein the compound bearing nitrated phenyl groups is keyhole limpet hemocyanin bearing 2,4,6-trinitrophenyl groups.

22. A test kit for the qualitative or quantitative determination of SAP, comprising an organic or inorganic carrier coated with a compound bearing nitrophenyl groups, a solution of enzyme-labelled or unlabelled monoclonal or polyclonal first antibodies binding SAP, and if said first antibodies are not labelled with an enzyme, a solution of polyclonal, enzyme-conjugated second antibodies binding said first antibodies, an enzyme substrate in solid or dissolved form a standard solutions of SAP a buffer solution, and a calcium salt in solid or dissolved form.

23. A test kit according to claim 22, wherein said carrier coated with keyhole limpet hemocyanin bearing 2,4,6-trinitrophenyl groups.

24. A method of purification of SAP, comprising mixing a solution containing SAP with a calcium salt to form a firt mixture, bringing said first mixture into contct with a solid carrier bearing nitrated phenyl groups washing away unbound proteins and other impurities with aqueous solutions containing calcium ions, and eluting said SAP with an aqueous solution containing a calcium chelator, with aqueous acids or buffer solutions in a pH range below pH 5, or with buffer solutions containing p-nitrophenylarsonic acid.

* * * * *